United States Patent
Rubin

(12) 
(10) Patent No.: US 6,384,038 B1
(45) Date of Patent: May 7, 2002

(54) METHODS AND COMPOSITIONS USING CETIRIZINE IN COMBINATION WITH LEUKOTRIENE INHIBITORS OR DECONGESTANTS

(75) Inventor: Paul D. Rubin, Sudbury, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/059,571

(22) Filed: Apr. 14, 1998

(51) Int. Cl.$^7$ ............................................. A61K 31/495
(52) U.S. Cl. ...................... 514/255; 514/826; 514/849; 514/850; 514/853; 514/860; 514/862; 514/887
(58) Field of Search ................................ 514/255, 826, 514/849, 850, 853, 860, 862, 887

(56) References Cited

U.S. PATENT DOCUMENTS

| | | | | |
|---|---|---|---|---|
| 4,581,232 A | * | 4/1986 | Peters et al. ................ | 424/155 |
| 4,783,465 A | * | 11/1988 | Sunshine et al. ........... | 514/255 |
| 5,276,044 A | * | 1/1994 | Ambrus et al. ............. | 514/352 |
| 5,478,941 A | * | 12/1995 | Cossement et al. ......... | 544/383 |

FOREIGN PATENT DOCUMENTS

| | | |
|---|---|---|
| EP | 780127 A1 | 6/1997 |
| WO | WO 97/28797 | 8/1997 |
| WO | 99/32125 | 7/1999 |

OTHER PUBLICATIONS

Ganse et al, "Effects of antihistamines in adult asthma: a meta–analysis of clinical trials", Eur. Respir. J. (10), pp. 2216–2224 (1997).*

Stater et al, "Second–Generation Antihisamines: a Comparative Review", Drugs 57(1), pp. 31–47 (1999).*

Baroody, F.M., et al., "Effects of Loratadine and Terfenadine on the Induced Nasal Allergic Reaction", Arch. Otolaryngol. Head and Neck Surg., 122:309–316 (1996).

F–D–C Reports, "Trade and Govt. Memos", Feb. 9, 1998.

Ku, Y., et al., "Effects of Histamine $H_1$ Receptor Antagonists on Action Potentialists in Guinea–Pig Isolated Papillary Muscles", Arch. Int. Pharmacodyn., 331:59–73 (1996).

Merk Index, "6340, Montelukast," p. 1070, Twelfth Edition (1996).

Physician's Desk Reference, p. 303, 474–476,3148–3149 (1988).

Roquet, A., et al., "Combined Antagonism of Leukotriene and Histamine Produces Predominant Inhibition of Allergen–Induced Early and Late Phase Airway Obstruction in Asthmatics", Am. J. Respir. Crit. Care Med., 155:1856–1863 (1997).

Zhang, M.Q., & Timmerman, H., "Leukotriene $cysLT_1$ ($LTD_4$) receptor antagonism of $H_1$–antihistamines: An in vitro study", Inflamm. Res., 46(1):S93–S94 (1997).

Joelson I. Braga da Motta et al., Drug Modulation of Antigen–induced paw Oedema in Guinea–Pigs: Effects of Lipopolysaccharide, Tumor Necrosis Factor and Leucocyte Depletion, Br. J. Pharmacol. (1994), 112, 111–116.

* cited by examiner

Primary Examiner—Frederick Krass
(74) Attorney, Agent, or Firm—Pennie & Edmonds LLP

(57) ABSTRACT

Methods and pharmaceutical compositions employing (+) cetirizine, (–) cetirizine, or racemic cetirizine, or a pharmaceutically acceptable salt thereof, and a leukotriene inhibitor, or a pharmaceutically acceptable salt thereof, or decongestant for the treatment, management, and/or prevention of inflammation, asthma or symptoms thereof, allergic disorders such as allergic rhinitis, and dermatitis.

7 Claims, No Drawings

METHODS AND COMPOSITIONS USING CETIRIZINE IN COMBINATION WITH LEUKOTRIENE INHIBITORS OR DECONGESTANTS

FIELD OF THE INVENTION

The invention relates to methods of prevention and treatment using, and pharmaceutical compositions containing, cetirizine and a leukotriene inhibitor.

BACKGROUND OF THE INVENTION

In its racemic form, cetirizine, chemically named 2-[4-[(4-chlorophenyl)-phenylmethyl]-1-piperazinyl]ethoxy] acetic acid, is an orally active, potent, long acting peripheral histamine $H_1$ receptor antagonist. See, e.g., Juhlin, L., et al. *J. Allergy Clin. Immunol.* 80:599–602 (1987); De Vos, C., et al. *Annal. Allergy* 59:278–282 (1987); U.S. Pat. No. 4,525,358. Cetirizine is a second generation $H_1$ histamine receptor antagonist that generally offers some significant advantages beyond the first generation compounds. These advantages include: (1) less sedation, (2) little anticholinergic activity, and (3) longer duration of activity. The medicinal chemistry of cetirizine is described by Campoli-Richards et al., *Drugs* 40:762–781 (1990), Snyder and Snowman, *Allergy* 59II:4–8 (1987), and Rihoux and DuPont, *Annals of Allergy* 59:235–238 (1987).

Cetirizine has been employed in the treatment of some symptoms of allergic reactions. For example, U.S. Pat. No. 5,419,898 to Ikejiri et al. discloses antiallergic compositions containing cetirizine for ophthalmic or nasal use. Its efficacy in the treatment of some other symptoms associated with asthma, however, is limited. Specifically, clinical studies conducted by Gong and coworkers revealed that the compound, when administered to patients in doses as large as 20 mg, is not uniformly effective in preventing allergen- or exercise-induced bronchoconstriction (Gong, H., et al. *J. Allergy Clin. Immunol.* 85:632–641 (1990)).

In only a few cases has cetirizine been combined with other drugs for the treatment of disease. For example, U.S. Pat. No. 4,829,064 to Sunshine et al. discloses compositions useful for treating cold symptoms comprising cetirizine and an analgesic. Published European Pat. Application No. 433766 A1 to York et al. discloses compositions of cetirizine and an antiallergic compound useful for treating ophthalmic allergic responses.

Although the stereoselectivity of some drugs is well known (see, e.g., Ariens, E. J. Schweiz. Med. Wocheuschr. 120:131–134 (1994)), disclosures directed to the combination of cetirizine with other drugs have taught away from combinations comprising optically pure enantiomers of cetirizine. Recently, however, some advantages of treating certain diseases with an optically pure enantiomer of cetirizine alone has been recognized.

U.S. Pat. No. 5,627,183 discloses methods of treating urticaria using optically pure (+) cetirizine. U.S. Pat. No. 5,698,558 discloses methods of treating certain allergic disorders using (−) cetirizine. Both patents disclose that the administration of optically pure enantiomers of cetirizine can reduce or avoid adverse side effects associated with the use of racemic cetirizine. These side effects include sedation and somnolence, headache, gastrointestinal disturbance, dizziness, nausea, cardiac arrhythmias, and other cardiovascular effects. Such adverse effects are common to non-sedating antihistamines.

It has been suggested that the moderate effectiveness of some $H_1$-antihistamines is due in part to their additional activity against leukotrienes, particularly leukotriene $D_4$ ($LTD_4$). Leukotrienes augment neutrophil and eosinophil migration, neutrophil and monocyte aggregation, leukocyte adhesion, increase capillary permeability, and smooth muscle contraction, all of which contribute to inflammation, edema, mucus secretion, and bronchoconstriction.

In one study of guinea pigs, the increase in airway resistance caused by $LTD_4$ was suppressed by the antihistamine terfenadine. See Akagi et al., Oyo Yakuri, 35: 361–371 (1988). In another study, twenty $H_1$-antihistamines with diverse chemical structures were tested for activity against $LTD_4$-induced contraction in isolated guinea-pig ileum and displacement of [$^3$H]$LTD_4$ from guinea-pig lung membrane proteins (M. Zhang et al., Inflamm. res. 46:Supp. I S93-S94 (1997)). The results indicated the drugs were weakly active in inhibiting $LTD_4$-induced contraction of guinea pig ileum.

A number of drugs have been designed specifically to inhibit leukotriene formation. One of these, zileuton, is a specific inhibitor of 5-lipoxygenase. Commercially available as ZYFLO®, it has the chemical name (±)-1-(1-Benso[b]thien-2-ylethyl)-1-hydroxyurea. Zileuton is known to inhibit leukotriene ($LTH_4$, $LTC_4$, $LTD_4$, and $LTE_4$) formation in vitro. Zileuton is an inhibitor ex vivo of $LTB_4$ formation in several species and inhibits leukotriene-dependent smooth muscle contractions in vitro in guinea pig and human airways. One study of 373 patients indicated that 600 mg of zileuton four times daily were required to provide efficacy, while 400 mg failed to do so. In some patients, zileuton was reported to cause headache, pain, asthenia, dyspepsia, nausea, and myalgia (*Physician's Desk Reference*, 52 ed., Medical Economics Co., Inc., 474–76 (1998)).

Zafirlukast, sold commercially as ACCOLATE®, is another type of leukotriene inhibitor. This leukotriene inhibitor is a leukotriene receptor antagonist (LTRA) of leukotriene $D_4$ and $E_4$, and has the chemical name 4-(5-cyclopentyloxy-carbonylamino-1-methyl-indol-8-ylmethyl)-3-methoxy-N-o-tolylsulfonylbenzamide. Cysteinyl leukotriene production and receptor occupation have been correlated with the pathophysiology of asthma. In vitro studies indicated that zafirlukast antagonized the contractile activity of three leukotrienes in conducting airway smooth muscle from laboratory animals and humans; prevented intradermal $LTD_4$-induced increases in cutaneous vascular permeability; and inhibited inhaled $LTD_4$-induced influx of eosinophils into animal lungs. In some patients, zafirlukast has been reported to cause headache, infection, nausea, diarrhea, pain, asthenia, abdominal pain, dizziness, myalgia, fever, vomiting, SGPT elevation, and dyspepsia (*Physician's Desk Reference*, 52 ed., Medical Economics Co., Inc., 3148–49 (1998)).

SUMMARY OF THE INVENTION

The present invention represents an improvement over both the cetirizine and the leukotriene inhibitor technology presently available.

This invention relates to novel pharmaceutical compositions comprising: (a) an optically pure enantiomer of cetirizine, a racemic mixture of cetirizine, or a pharmaceutically acceptable salt thereof; and (b) a leukotriene inhibitor. These compositions may optionally contain an additional ingredient, such as a decongestant.

The compositions of the present invention are believed to improve upon, and are superior to, those of the prior art used to treat or prevent asthma, asthma symptoms, inflammation, allergic disorders such as allergic rhinitis, and dermatitis. Unexpectedly, it is believed that there is a synergistic effect when cetirizine, or an enantiomer or salt thereof, is used in combination with one or more leukotriene inhibitors. Both racemic and optically pure enantiomers of cetirizine may be used to achieve this synergistic effect. Furthermore, the compositions and methods of this invention avoid or reduce certain adverse side effects associated with second generation $H_1$ histamine receptor antagonists.

The compositions of this invention possess potent antihistaminic activity. They are useful for treating and preventing the occurrence of asthma or asthma symptoms. They are also useful for the treatment and prevention of dermatitis, inflammation, and allergic disorders such as allergic rhinitis. The compositions of this invention may also be used to threat the symptoms of allergic asthma, allergic rhinitis, and other allergic disorders, as well as dermatitis. In addition, the compositions of the invention reduce or avoid adverse effects generally associated with administration of non-sedating antihistamines, such as racemic cetirizine or an enantiomer of cetirizine. Adverse effects include, but are not limited to, cardiac arrhythmias, drowsiness, nausea, fatigue, weakness and headache.

The compositions of this invention are also useful in combination with non-steroidal anti-inflammatory agents or other non-narcotic analgesics for the treatment or prevention of inflammation, cough, cold, cold-like, and/or flu symptoms and the discomfort, headache, pain, fever, and general malaise associated therewith. The aforementioned combinations (e.g., an enantiomer or racemic mixture of cetirizine and a leukotriene inhibitor) may optionally include one or more other active components including a decongestant, cough suppressant/antitussive, or expectorant.

Additionally, the novel pharmaceutical compositions of the invention are useful in treating, preventing, or managing motion sickness, vertigo, diabetic retinopathy, small vessel complications due to diabetes and such other conditions as may be related to the activity of these derivatives as antagonists of the $H_1$ histamine receptor. The compositions can be used to treat or prevent these disorders while reducing or avoiding adverse effects associated with administration of non-sedating antihistamines.

In one embodiment, this invention provides for a method of treating or preventing asthma or asthma symptoms in a human which comprises administering to a human a therapeutically effective amount of an optically pure enantiomer of cetirizine, racemic cetirizine, or a pharmaceutically acceptable salt thereof, and a therapeutically effective amount of a leukotriene inhibitor, or a pharmaceutically acceptable salt thereof. Preferably, the leukotriene inhibitor is a 5-lipoxygenase inhibitor or a 5-lipoxygenase activating protein antagonist.

The invention also provides a method of treating or preventing asthma or asthma symptoms in a human comprising administering to a human a composition, said composition comprising (i) a therapeutically effective amount of an optically pure enantiomer of cetirizine, racemic cetirizine, or a pharmaceutically acceptable salt thereof; (ii) a leukotriene inhibitor, or a pharmaceutically acceptable salt thereof, selected from the group consisting of 5-lipoxygenase inhibitors, 5-lipoxygenase activating protein antagonists, and leukotriene receptor antagonists; and a pharmaceutically acceptable carrier or excipient.

This invention is further directed to a method of treating or preventing asthma or the symptoms of asthma in a human which comprises administering to a human therapeutically effective amounts of an optically pure enantiomer of cetirizine, racemic cetirizine, or a pharmaceutically acceptable salt thereof, a leukotriene inhibitor, or a pharmaceutically acceptable salt thereof, and a decongestant. Preferably, the leukotriene inhibitor is a 5-lipoxygenase inhibitor or a 5-lipoxygenase activating protein antagonist.

In a second embodiment, the invention provides for a method of treating or preventing dermatitis in a human which comprises administering to a human a therapeutically effective amount of an optically pure enantiomer of cetirizine, racemic cetirizine, or a pharmaceutically acceptable salt thereof, and a leukotriene inhibitor, or a pharmaceutically acceptable salt thereof.

In a third embodiment, the invention provides for a method of treating or preventing allergic rhinitis in a human which comprises administering to a human a therapeutically effective amount of an optically pure enantiomer of cetirizine, racemic cetirizine, or a pharmaceutically acceptable salt thereof, and a leukotriene inhibitor, or a pharmaceutically acceptable salt thereof. Preferably, the leukotriene inhibitor is a 5-lipoxygenase inhibitor or a 5-lipoxygenase activating protein antagonist.

In a fourth embodiment, the invention provides for a method of treating or preventing inflammation in a human which comprises administering to a human a therapeutically effective amount of an optically pure enantiomer of cetirizine, racemic cetirizine, or a pharmaceutically acceptable salt thereof, and a leukotriene inhibitor, or a pharmaceutically acceptable salt thereof.

In a fifth embodiment, the invention provides for a method of preventing or treating a condition responsive to leukotriene inhibition which comprises administering to a human a therapeutically effective amount of cetirizine, or a pharmaceutically acceptable salt thereof, a leukotriene inhibitor, or a pharmaceutically acceptable salt thereof, and optionally a decongestant, or a pharmaceutically acceptable salt thereof.

The invention encompasses the treatment, prevention, and/or management of these disorders using a single unit dosage form that contains an optically pure enantiomer of cetirizine or racemic cetirizine, or a pharmaceutically acceptable salt thereof, and a leukotriene inhibitor, or a pharmaceutically acceptable salt thereof, such that the cetirizine component and leukotriene inhibitor are in one solid or liquid dosage form. It should be recognized, however, that combination therapy by separate administration of each active ingredient is also contemplated. Consequently, the administration of the active ingredients (i.e., optically pure or racemic cetirizine and leukotriene inhibitor, and optionally decongestant) of this invention may be concurrent or sequential. For example, a cetirizine component and a leukotriene inhibitor may be administered as a combination, concurrently but separately, or by the sequential administration of cetirizine and leukotriene inhibitor or the sequential administration of a leukotriene inhibitor and cetirizine. Cetirizine may be administered in a similar manner with a decongestant.

DETAILED DESCRIPTION OF THE INVENTION

The present invention encompasses the treatment, prevention, and/or management of asthma, the symptoms of asthma, dermatitis, inflammation, or allergic disorders, such as allergic rhinitis, using an optically pure enantiomer of cetirizine or racemic cetirizine, or a pharmaceutically acceptable salt thereof, in combination with a leukotriene inhibitor; and optionally a decongestant.

According to the present invention, all means of treatment, prevention, and/or management of these disorders, including, but not limited to, topical, local, and systemic, may employ racemic cetirizine, optically pure (+) cetirizine or (−) cetirizine, or a pharmaceutically acceptable salt thereof. It is preferred, however, that (+) cetirizine, or a pharmaceutically acceptable salt thereof, in combination with a leukotriene inhibitor, and optionally a decongestant, be used for the topical or local treatment, prevention, and/or management of dermatitis, inflammation, or related disorders. It is preferred that (−) cetirizine, or a pharmaceutically acceptable salt thereof, be used in combination with a leukotriene inhibitor, and optionally a decongestant, for the systemic treatment of asthma, the symptoms of asthma, or allergic disorders, such as allergic rhinitis.

Without being limited by theory, it is believed that (−) cetirizine generally has a lower affinity towards the cortex $H_1$ histamine receptor than (+) cetirizine. Consequently, the administration of (−) cetirizine in combination with a leukotriene inhibitor and optionally a decongestant may have fewer undesirable effects on the central nervous system, such as sedation or drowsiness, than would result from administration of the corresponding (+) cetirizine combination. At the same time, (+) cetirizine is able to inhibit the effects of histamine present in high local concentrations. For at least this reason, topical or local treatment, prevention, and/or management of inflammation and other disorders may be more effective with the administration of (+) cetirizine in combination with a leukotriene inhibitor and optionally a decongestant than with the administration of the corresponding (−) cetirizine combination.

It should be recognized that the invention includes the use of the cetirizine active ingredient and the leukotriene inhibitor as a combination either in a single composition, or separately but concurrently and/or sequentially. The same is true when an optional decongestant is used.

The methods and compositions of this invention are believed to reduce or avoid adverse effects associated with administration of non-sedating antihistamines, and particularly with administration of racemic cetirizine alone. The methods and compositions described herein are believed to provide superior or improved therapy over prior art methods and compositions involving optically pure or racemic cetirizine in the absence of a leukotriene inhibitor, or a leukotriene inhibitor in the absence of optically pure or racemic cetirizine. Without being limited by theory, it is believed that the combination of optically pure or racemic cetirizine, or a pharmaceutically acceptable salt thereof, a leukotriene inhibitor, or a pharmaceutically acceptable salt thereof, and optionally a decongestant, provides superior, improved, and synergistic effects unachievable by any of these compounds alone.

The preparation of racemic cetirizine can be performed by the methods described in U.S. Pat. No. 2,899,436 to Morren et al., U.S. Pat. No 4,525,358 to Bates et al., or by an improved procedure described in British Application No. 2,225,320 of Cossement et al., the disclosures of which are hereby expressly incorporated herein by reference thereto for this purpose. Synthesis of substantially optically pure (+) and (−) enantiomers of cetirizine is described in British Application No. 2,225,320 of Cossement et al., as well as in U.S. Pat. No. 5,478,941 to Cossement et al., the disclosures of which are also expressly incorporated herein by reference thereto. Alternatively, the optically pure enantiomers can be resolved from the racemic mixture using standard techniques available in the art.

As used herein, the terms "adverse effects" and "adverse side effects" include, but are not limited to, cardiac arrhythmias, cardiac conduction disturbances, appetite stimulation, weight gain, sedation, gastrointestinal distress, headache, dry mouth, constipation, and diarrhea. The term "cardiac arrhythmias" includes, but is not limited to, ventricular tachyarrhythmias, torsades de pointes, and ventricular fibrillation.

The term "asthma" as used herein is defined as a disorder characterized by increased responsiveness of the trachea and bronchi to various stimuli, which results in symptoms that include, but are not limited to, wheezing, cough, shortness of breath, dyspnea, and the like. Asthma includes, for example, allergic asthma.

The term "dermatitis" as used herein is that disorder caused by inflammation to the skin including endogenous and contact dermatitis such as, but not limited to: actinic dermatitis (or photodermatitis), atopic dermatitis, chemical dermatitis, cosmetic dermatitis, dermatitis aestivalis, and seborrheic dermatitis.

As used herein, the term "pharmaceutically acceptable salt" refers to a salt prepared from pharmaceutically acceptable non-toxic acids or bases including inorganic acids or bases or organic acids or bases. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), lysine and procaine.

The terms "substantially optically pure," "optically pure," and "optically pure enantiomers" as used herein mean that the composition contains greater than about 95% of the desired enantiomer by weight, preferably greater than about 98% of the desired enantiomer by weight, and most preferably greater than about 99% of the desired enantiomer by weight, said percent based upon the total weight of cetirizine. In other words, the term "substantially free" means less than about 5 weight percent, preferably less than about 2 weight percent, and more preferably less than about 1 weight percent.

The term "cetirizine" when used without modification means the compound in all its forms, including, but not limited to, racemic cetirizine, optically pure enantiomers of cetirizine, and mixtures thereof.

The term "racemic" as used herein means a mixture of the (+) and (−) enantiomers of a compound wherein the (+) and (−) enantiomers are present in approximately a 1:1 ratio.

The phrase "therapeutically effective amount of cetirizine" as used herein means that amount of optically pure or racemic cetirizine, or a pharmaceutically acceptable salt thereof, which, alone or in combination with other drugs, provides a therapeutic benefit in the treatment, management, or prevention of conditions that are responsive to histamine antagonists, such as asthma, asthma symptoms, allergic disorders such as allergic rhinitis, and dermatitis.

The phrase "therapeutically effective amount of leukotriene inhibitor" as used herein means that amount of leukotriene inhibitor which alone, or in combination with other drugs, provides a therapeutic benefit in the treatment, management, or prevention of any condition that is responsive to leukotriene inhibitors, such as asthma, asthma symptoms, inflammation, allergic disorders such as allergic rhinitis, and dermatitis.

The phrase "therapeutically effective amount of a decongestant" as used herein means that amount of decongestant which alone, or in combination with other drugs, provides a therapeutic benefit in the treatment, management, or prevention of congestion of the respiratory tract and/or sinus.

The term "leukotriene inhibitor" as used herein includes any agent or compound that inhibits, restrains, retards or otherwise interacts with the action or activity of leukotrienes, such as, but not limited to, 5-lipoxygenase ("5-LO") inhibitors, 5-lipoxygenase activating protein ("FLAP") antagonists, and leukotriene receptor antagonists ("LTRAs").

The term "5-lipoxygenase inhibitor" or "5-LO inhibitor" as used herein includes any agent or compound that inhibits, restrains, retards or otherwise interacts with the enzymatic action of 5-lipoxygenase, such as, but not limited to, zileuton, docebenone, piripost, and ICI-D2318.

The term "5-lipoxygenase activating protein antagonist" or "FLAP antagonist" as used herein includes any agent or compound that inhibits, restrains, retards or otherwise interacts with the action or activity of 5-lipoxygenase activating protein, such as, but not limited to, MK-591 and MK-886.

The term "leukotriene receptor antagonist" or "LTRA" as used herein includes any agent or compound that inhibits, restrains, retards or otherwise antagonizes the activity of receptors that are responsive to leukotrienes, including those responsive to leukotriene $D_4$. Exemplary LTRAs include sodium 1-(((R)-(3-(2-(6,7-difluoro-2-quinolinyl) -ethenyl) phenyl)-3-(2-(2-hydroxy-2-propyl)phenyl)thio)methyl)-cyclopropaneacetate, 1-(((1(R)-(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid or salts thereof, pranlukast, zafirlukast (ICI-204219), and montelukast (MK-476), the latter of which is sold commercially as SINGULAIR®.

The magnitude of a prophylactic or therapeutic dose of optically pure or racemic cetirizine or leukotriene inhibitor in the acute or chronic prevention, treatment, or management of a disorder or condition will vary with the severity of the condition to be treated and the route of administration. The dose, and perhaps the dose frequency, will also vary according to the age, body weight, and response of the individual patient. The magnitude of the dose may also depend upon whether optically pure or racemic cetirizine is used. Furthermore, if an optically pure enantiomer of cetirizine is used, the magnitude of the dose may depend upon whether it is the (+) or (−) enantiomer. Suitable total daily dose ranges can be readily determined by those skilled in the art. In general, the total daily dose range for optically pure or racemic cetirizine, for the conditions described herein, is from about 0.01 mg to about 50 mg administered in single or divided doses. For example, a preferred oral daily dose range should be from about 1 mg to about 30 mg. A more preferred oral dose is about 5 mg to about 25 mg. A preferred oral daily dose range of decongestant, such as pseudoephedrine, should be from about 50 mg to about 300 mg, more preferably, about 150 mg to about 250 mg. In addition, suitable oral daily dosage ranges of leukotriene inhibitor can be readily determined by those skilled in the art (see, e.g., *Physician's Desk Reference*). For example, for 5-lipoxygenase inhibitors, a preferred oral daily dose range of leukotriene inhibitor should typically be from about 20 mg to 2,500 mg, preferably about 20 mg to 800 mg. For leukotriene receptor antagonists, a preferred oral daily dose of leukotriene inhibitor should typically be from about 2 mg to 100 mg, preferably about 5 mg to 20 mg.

It is further recommended that children, patients aged over 65 years, and those with impaired renal or hepatic function initially receive low doses, and that they then be titrated based on individual response (s) or blood level (s). It may be necessary to use dosages outside these ranges in some cases as will be apparent to those skilled in the art. Further, it is noted that the clinician or treating physician will know how and when to adjust, interrupt, or terminate therapy in conjunction with individual patient response.

Any suitable route of administration may be employed for providing the patient with an effective dosage of an optically pure or racemic cetirizine and leukotriene inhibitor according to the methods of the present invention. For example, oral, intraoral, rectal, parenteral, epicutaneous, transdermal, subcutaneous, intramuscular, intranasal, sublingual, buccal, intradural, intraocular, intrarespiratory, or nasal inhalation and like forms of administration may be employed. Oral administration is generally preferred. For the methods to treat dermatitis, however, topical administration is preferred.

The pharmaceutical compositions used in the methods of the present invention, which are sterile and stable, include optically pure or racemic cetirizine, or a pharmaceutically acceptable salt thereof, a leukotriene inhibitor, or a pharmaceutically acceptable salt thereof, and optionally a decongestant, as the active ingredient. The compositions may also contain a pharmaceutically acceptable carrier or excipient, and, optionally, other therapeutic ingredients.

The compositions for use in the methods of the present invention can include suitable excipients or carriers such as starches, sugars, microcrystalline cellulose, diluents, granulating agents, lubricants, binders, disintegrating agents, and the like.

Dosage forms include tablets, troches, dispersions, suspensions, solutions, capsules, patches, gel caps, syrups, elixirs, gels, powders, magmas, lozenges, ointments, creams, pastes, plasters, lotions, discs, suppositories, nasal or oral sprays, aerosols, and the like.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are expressly incorporated herein by reference thereto.

Pharmaceutical compositions for use in the methods of the present invention may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients.

Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

The invention is further defined by reference to the following examples describing in detail the preparation of the composition and the compositions used in the methods of the present invention, as well as their utility. It will be apparent to those skilled in the art that many modifications, both to materials and methods, may be practiced which are within the scope of this invention.

EXAMPLES

Synthesis of Racemic Cetirizine

The dihydrochloride salt of (±)2-[2-[-4-[(4-chlorophenyl)phenylmethyl]-1-piperazinyl]ethoxy]-acetic acid may be prepared according to the method of Cossement et al., disclosed in British Patent Application No. 2,225,321.

In 250 ml of ethanol, 23 g (0.062 mole) of racemic 2-[2-[-4-[(4-chlorophenylmethyl]-1-piperazinyl]ethoxy]acetonitrile and 31 ml of a 4N ethanolic solution of potassium hydroxide are introduced successively into a three-necked round-bottomed flask equipped with a mechanical stirrer, a condenser and a thermometer. The reaction mixture is refluxed for 10 hours, while stirring. It is then allowed to cool and its pH is brought to 6 by addition of 37% concentrated hydrochloric acid. The ethanol is evaporated and the reaction mixture is diluted with 100 ml of water and extracted three times with 200 ml of dichloromethane.

The organic phases are combined, dried over magnesium sulphate, filtered, and concentrated in a rotary evaporator. An oil is obtained and is allowed to crystallize by addition of 100 ml of 2-butanone, while hot. The solid formed is filtered, washed, and dried to obtain 18.9 g of racemic 2-[2-[-4-[(4-chlorophenyl)phenylmethyl]-1-piperazinyl]ethoxy]acetic acid.

The acid is resuspended in 150 ml of water, the pH of which is brought to 0.8 by addition of concentrated hydrochloric acid. The aqueous solution is concentrated on a rotary evaporator and the residue is then diluted by addition of 75 ml of 2-butanone. This induces crystallization of racemic 2-[2-[-4-[(4-chlorophenyl)phenylmethyl]-1-piperazinyl]ethoxy]-acetic acid dihydrochloride. The crystals are filtered off and dried to yield 21.7 g (75.9%) of product. The melting point of the crystals is 220.15° C. as measured by differential scanning calorimetry (DSC).

Alternative Synthesis of Racemic Cetirizine

Alternatively, (±)2-[2-[-4-[(4-chlorophenyl)phenylmethyl]-1-piperazinyl]ethoxy]-acetic acid may be prepared according to the method of Baltes et al. disclosed in U.S. Pat. No. 4,525,358. In this method, 2-[2-[4-Diphenylmethyl)-1-piperazinyl]ethoxy]-acetamide dihydrochloride is first synthesized as follows:

A mixture of 37.8 g (0.15 mole) of 1-(diphenylmethyl)-piperazine, 27.5 g (0.2 mole of 2-(2-chloroethoxy)-acetamide and 26.5 g of anhydrous sodium carbonate in 120 ml of xylene is heated for 4 hours to 90° C. to 120° C. Thereafter, 120 ml of benzene are added to the reaction mixture, the precipitate formed is filtered off and the organic phase is extracted with dilute hydrochloric acid (30 ml of concentrated hydrochloric acid and 100 ml of water). 40 ml of a concentrated aqueous solution of sodium hydroxide are added, followed by extraction with benzene. The benzene solution is washed with water, dried over anhydrous sodium carbonate and the benzene is evaporated off to dryness. The evaporation residue is titrated with diethyl ether and left to crystallize. 2-[2-[4-Diphenylmethyl)-1-piperazinyl]ethoxy] acetamide is obtained in a yield of 73% (M.P. 119° C.–120° C).

In the second part of the synthesis, a mixture of 19 g (0.054 mole) of 2-[2-[4-diphenylmethyl)-1-piperazinyl] ethoxy]-acetamide in 200 ml of ethanol and 27 ml of a 4 N ethanolic solution of sodium hydroxide is heated under reflux for 3 hours. The reaction mixture is adjusted with 29.7 ml of 3.61 N hydrochloric acid to a pH of 6.3, whereafter the ethanol is evaporated off in a vacuum. The precipitate obtained is filtered off. After evaporation of the solvent, 17.4 g of crude 2-[2-[4-diphenylmethyl)-1-piperazinyl]ethoxy]-acetic acid are obtained (yield=91%; M.P. 100° C.). This product may be purified by conventional means known to those skilled in the art.

Synthesis of Optically Pure (+) Cetirizine

The dihydrochloride salt of (+)2-[2-[-4-[(4-chlorophenyl)phenylmethyl]-1-piperazinyl]ethoxy]-acetic acid may be prepared according to the method of Cossement et al. disclosed in British Patent Application No. 2,225,321.

9.42 g (0.0255 mole) of levorotatory 2-[2-[4-[(4-chlorophenyl)phenylmethyl]-1--piperazinyl]ethoxy]-acetonitrile are introduced into a reactor equipped with a mechanical stirrer, a condenser, a thermometer, and a dropping funnel and are heated to 45° C., while stirring. 15 ml of 37% concentrated hydrochloric acid are then added. The temperature of the reaction mixture rises to 92° C. The temperature of the reaction mixture is maintained at 60° C. for 60 minutes while stirring. The reaction mixture is allowed to cool and is concentrated on a rotary evaporator. The residue is then taken up in 50 ml of water. The pH of the reaction mixture is brought to 5 by addition of sodium hydroxide and the mixture is extracted with several successive fractions of dichloromethane. The organic phases are combined and dried over magnesium sulphate and the solvent is removed on a rotary evaporator. 9.6 g of the free acid of the final product are thus obtained in the form of a beige powder, which are then converted into the dihydrochloride by means of a solution of hydrochloric acid in acetone. The dihydrochloride is crystallized from this solution. After filtration and drying, 9.8 g of (+)2-[2-(4-[(4-chlorophenyl)phenylmethyl)-1-piperazinyl]ethoxy]-acetic acid dihydrochloride are obtained. The purity of this product, obtained in 83% yield, may be measured by high performance liquid chromatography with a chiral stationary phase of a $\alpha_1$-AGP (from the LKB Company). It is typically 95% with respect to the dextrorotatory enantiomer. The product has a melting point of 199–201° C. (224.4° C. as measured by DSC), and an [α] of +9.4° (c=1, water).

Synthesis of Optically Pure (−) Cetirizine

This product is obtained by the method described in example 5.3, but starting from dextrorotatory 1-[(4-chlorophenyl)phenylmethyl)-piperazine, the latter being obtained by treating the racemate with (2S, 3S)-tartaric acid using techniques known to those skilled in the art.

The dihydrochloride salt of (−)2-[2-[-4-[(4-chlorophenyl)phenylmethyl]-1-piperazinyl]ethoxy]-acetic acid is obtained in yields and with a purity very close to those obtained for the dextrorotatory acid dihydrochloride: 95% measured by high performance liquid chromatography with a chiral stationary phase of $\alpha_1$-AGP (from the LKB Company). The product has a melting point of 198–200° C. (220.7° C. as measured by DSC), but decomposes upon melting.

While the present invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method for the prophylaxis or treatment of asthma or a symptom thereof in a human which comprises administering to a human in need thereof:

(a) a therapeutically effective amount of cetirizine or a pharmaceutically acceptable salt thereof, and;

(b) a therapeutically effective amount of a leukotriene inhibitor, or a pharmaceutically acceptable salt thereof.

2. A method for the prophylaxis or treatment of asthma or a symptom thereof in a human which comprises administering to a human, in need thereof, a composition comprising:

(a) a therapeutically effective amount of cetirizine or a pharmaceutically acceptable salt thereof;

(b) a therapeutically effective amount of a leukotriene inhibitor, or a pharmaceutically acceptable salt thereof, selected from the group consisting of 5-lipoxygenase inhibitors, 5-lipoxygenase activating protein antagonists, and leukotriene receptor antagonists, and mixtures thereof, and;

(c) a pharmaceutically acceptable carrier or excipient.

3. The method of claim 1 or 2 further comprising administering a therapeutically effective amount of a decongestant, or a pharmaceutically acceptable salt thereof.

4. The method of claim 1 or 2 wherein said human has asthma.

5. The method of claim 1 or 2 wherein said effective amount of cetirizine is an effective amount of racemic cetirizine.

6. The method of claim 1 or 2 wherein said cetirizine is the optically pure (+) enantiomer.

7. The method of claim 1 or 2 wherein said cetirizine is the optically pure (−) enantiomer.

* * * * *